United States Patent
Wales

(10) Patent No.: US 6,981,628 B2
(45) Date of Patent: Jan. 3, 2006

(54) SURGICAL INSTRUMENT WITH A LATERAL-MOVING ARTICULATION CONTROL

(75) Inventor: Kenneth S. Wales, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/615,972

(22) Filed: Jul. 9, 2003

(65) Prior Publication Data

US 2005/0006430 A1 Jan. 13, 2005

(51) Int. Cl.
*A61B 17/064* (2006.01)

(52) U.S. Cl. .................. 227/178.1; 227/175.1; 227/180.1

(58) Field of Classification Search ............ 227/19, 227/176.1, 180.1, 175.1; 606/205; 600/146
See application file for complete search history.

(56) References Cited

U.S. PATENT DOCUMENTS

| | | |
|---|---|---|
| 4,721,099 A | 1/1988 | Chikama |
| 5,405,344 A | 4/1995 | Williamson et al. |
| 5,465,895 A | 11/1995 | Knodel et al. |
| 5,553,765 A | 9/1996 | Knodel et al. |
| 5,575,799 A * | 11/1996 | Bolanos et al. ............ 606/139 |
| 5,588,581 A | 12/1996 | Conlon et al. |
| 5,643,294 A * | 7/1997 | Tovey et al. ............... 606/148 |
| 5,662,662 A * | 9/1997 | Bishop et al. ............. 606/143 |
| 5,673,840 A | 10/1997 | Schulze et al. |
| 5,704,534 A * | 1/1998 | Huitema et al. ......... 227/175.1 |
| 5,743,456 A * | 4/1998 | Jones et al. .............. 227/176.1 |
| 5,782,859 A * | 7/1998 | Nicholas et al. ............ 600/564 |
| 5,794,834 A * | 8/1998 | Hamblin et al. .......... 227/175.2 |
| 5,797,536 A | 8/1998 | Smith et al. |
| 5,797,538 A * | 8/1998 | Heaton et al. ........... 227/176.1 |
| 5,820,009 A * | 10/1998 | Melling et al. .......... 227/176.1 |
| 5,823,066 A * | 10/1998 | Huitema et al. ............... 74/527 |
| 5,829,662 A * | 11/1998 | Allen et al. .............. 227/177.1 |
| 5,855,311 A * | 1/1999 | Hamblin et al. ......... 227/176.1 |
| 6,241,139 B1 * | 6/2001 | Milliman et al. ........ 227/175.1 |
| 6,250,532 B1 | 6/2001 | Green et al. |
| 6,619,529 B2 * | 9/2003 | Green et al. ............. 227/176.1 |
| 6,631,837 B1 * | 10/2003 | Heck ....................... 227/176.1 |
| 6,644,532 B2 | 11/2003 | Green et al. |
| 2003/0045900 A1 | 3/2003 | Hahnen et al. |
| 2004/0050902 A1 | 3/2004 | Green et al. |

FOREIGN PATENT DOCUMENTS

| | | |
|---|---|---|
| EP | 0 593 920 A | 4/1994 |
| EP | 0 600 182 A | 6/1994 |
| WO | WO 01/00095 A | 1/2001 |

* cited by examiner

*Primary Examiner*—Rinaldi I. Rada
*Assistant Examiner*—Paul Durand
(74) *Attorney, Agent, or Firm*—Dean Garner

(57) ABSTRACT

An articulating surgical instrument suited for endoscopic use includes a lateral articulation control into a handle portion that provides an intuitive visual and tactile indication to the clinician as to the amount and direction of articulation of an end effector at a distal end of a shaft. Lateral movement of a lateral control actuator is converted into a longitudinal motion or a rotational motion transferred by the shaft to an articulation mechanism. A version of a lateral articulation control for a rotationally driven articulation mechanism incorporates an articulation backdrive lockout that prevents forces on the end effector from causing the selected amount of articulation from being changed.

13 Claims, 14 Drawing Sheets

SURGICAL INSTRUMENT WITH A LATERAL-MOVING ARTICULATION CONTROL

CROSS REFERENCE TO RELATED APPLICATIONS

The present application is related to four co-pending and commonly-owned applications filed on even date herewith, the disclosure of each is hereby incorporated by reference in their entirety, these four applications being respectively entitled:

(1) "SURGICAL INSTRUMENT INCORPORATING AN ARTICULATION MECHANISM HAVING ROTATION ABOUT THE LONGITUDINAL AXIS" to Kenneth S. Wales, Douglas B. Hoffman, Frederick E. Shelton IV, and Jeff Swayze;

(2) "SURGICAL STAPLING INSTRUMENT INCORPORATING AN ARTICULATION JOINT FOR A FIRING BAR TRACK" to Douglas B. Hoffman;

(3) "SURGICAL STAPLING INSTRUMENT HAVING ARTICULATION JOINT SUPPORT PLATES FOR SUPPORTING A FIRING BAR" to Kenneth S. Wales and Joseph Charles Hueil; and (4) "SURGICAL STAPLING INSTRUMENT INCORPORATING A TAPERED FIRING BAR FOR INCREASED FLEXIBILITY AROUND THE ARTICULATION JOINT" to Frederick E. Shelton IV, Mike Setser and Bruce Weisenburgh;

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and a energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician, this long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

Depending upon the nature of the operation, it may be desirable to further adjust the positioning of the end effector of an endoscopic surgical instrument rather than being limited to insertion and rotation. In particular, it is often desirable to orient the end effector at an axis transverse to the longitudinal axis of the shaft of the instrument. The transverse movement of the end effector relative to the instrument shaft is conventionally referred to as "articulation". This articulated positioning permits the clinician to more easily engage tissue in some instances. In addition, articulated positioning advantageously allows an endoscope to be positioned behind the end effector without being blocked by the instrument shaft.

While the aforementioned non-articulating stapling and severing instruments have great utility and may be successfully employed in many surgical procedures, it is desirable to enhance their operation with the ability to articulate the end effector, thereby giving greater clinical flexibility in their use. To that end, the four above cross-referenced applications disclose use of a rotational motion to articulate an end effector of a surgical stapling and severing instrument. A clinician rotates an outer control at the base of the shaft of the instrument to effect this articulation. In other articulating surgical instruments, articulation is generally effected by a longitudinal or rotational control input that is transferred as a longitudinal movement to the articulation joint. For instance, U.S. Pat. No. 6,241,139 describes a rotary control operably coupled to a stepped cam driver slot. Rotary motion of the control moves an intermediate piece containing the stepped cam driver slot laterally to articulate the end effector.

While these articulation controls do perform the intended function, it is believed that an enhanced articulation control may provide additional benefits. For instance, it would be desirable if the visual indication and tactile feel provided by the articulation control were intuitively understood by the clinician as to the expected direction and amount of articulation. In addition, it would be further desirable that the articulation control readily accept adjustment by the clinician yet resist a force on the end effector that may inadvertently change the amount of articulation. Furthermore, it would be further desirable that some versions of the articulation control be particularly suited for a surgical stapling and severing instrument that has a rotational motion down the shaft to effect articulation.

Consequently, a significant need exists for an improved articulation control for a surgical instrument.

BRIEF SUMMARY OF THE INVENTION

The invention overcomes the above-noted and other deficiencies of the prior art by providing an articulating surgical instrument that advantageously incorporates a lateral articulation control so that the user has an intuitive control of the articulation of an end effector. Such an instrument has particular utility in endoscopic use wherein the end effector is passed through a cannula passageway to a surgical site. Reaching the surgical site at a desired orientation, and perhaps being inserted behind other tissue, is facilitated by an articulation of the end effector from the longitudinal axis of a shaft. This task is assisted by the lateral articulation control providing an intuitive indication of the direction and amount of articulation of the end effector.

In one aspect of the invention, a surgical instrument that positions an end effector at a surgical site for performing a diagnostic or therapeutic treatment by inserting its shaft through a cannula passageway. The shaft advantageously includes an articulation motion transfer member that allows a clinician to articulate the end effector from a longitudinal axis of the shaft by controlling an articulation mechanism that pivotally couples the end effector to a distal end of the shaft. The user laterally positions an actuator to cause this articulation motion to be transferred through the shaft, with the lateral motion thereof converted into the articulation motion by a motion conversion mechanism. Thereby, the user receives an intuitive indication of which direction the end effector is articulated and the relative amount of articulation.

In another aspect of the invention, a surgical instrument performs articulation of the end effector by an articulation mechanism that responds to a rotational motion. A lateral articulation control again provides the intuitive control to a user by converting lateral motion into the rotational motion transferred through the shaft to the articulation mechanism.

In yet another aspect of the invention, a surgical instrument that is suitable endoscopic for such operations as stapling and severing by having three motions transferable to an end effector, specifically a firing motion, a closing motion, and an articulation motion. The lateral articulation control is positionable by the user to produce the articulation motion that causes the end effector to articulate. Since the end effector is remotely viewed by an endoscope that may be oriented from a different perspective than the user of the instrument, which may complicate visualizing the amount and direction of articulation of the end effector. However, the lateral articulation control proximate to a handle of the device gives the user this feedback.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
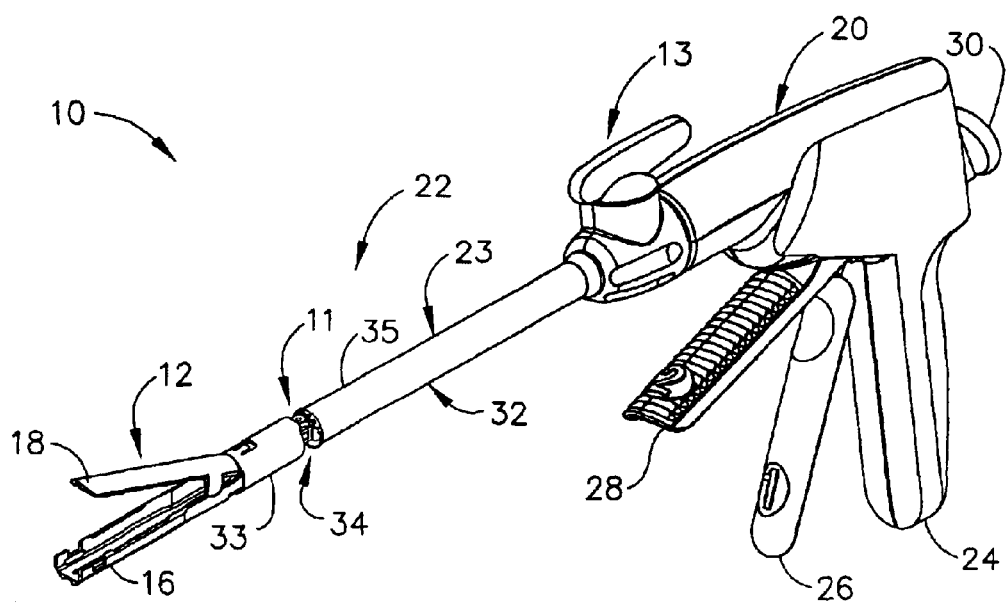
FIG. 1 is a perspective view of an articulating surgical instrument in a nonarticulated position.
Figure 2:
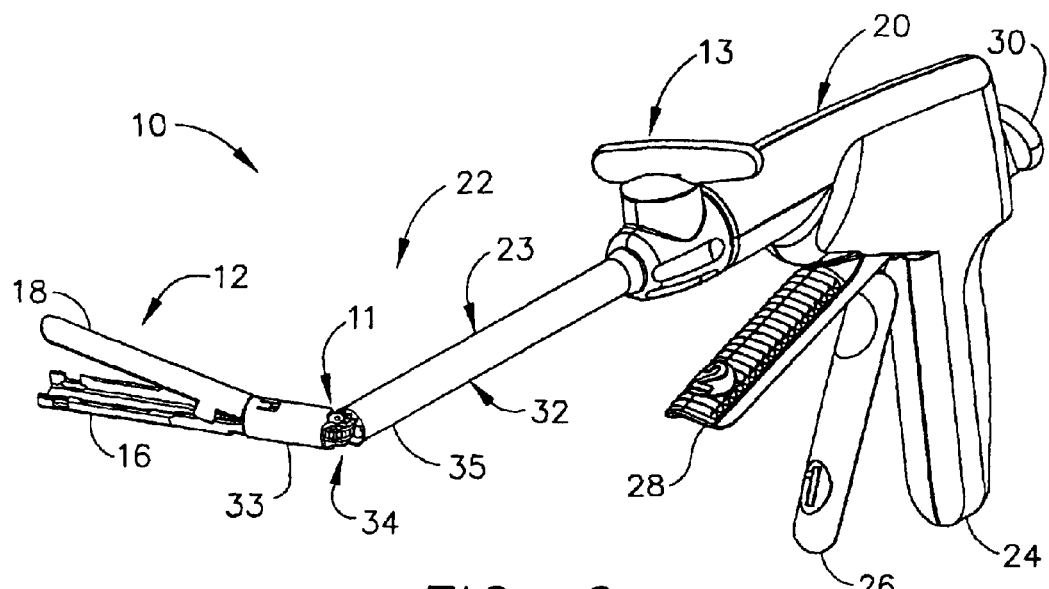
FIG. 2 is a perspective view of an articulating surgical instrument in an articulated position.
Figure 3:
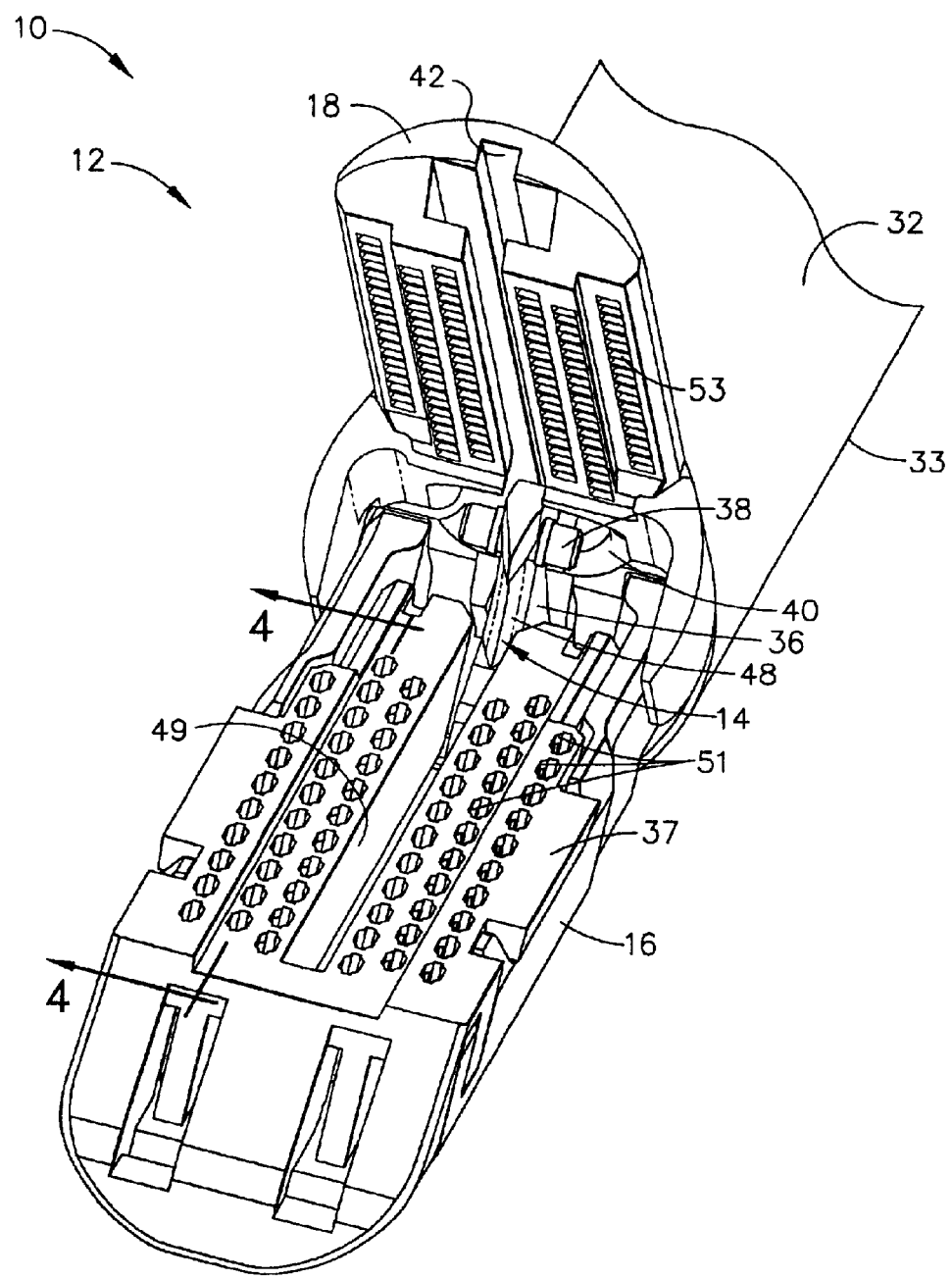
FIG. 3 is a perspective view of an opened end effector of the articulating surgical instrument of FIGS. 1–2.

Turning to the Drawings, wherein like numerals denote like components throughout the several views, FIGS. 1–3 depict a surgical instrument, which in the illustrative embodiment is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient for performing a surgical procedure. Once an articulation mechanism 11 and a distally attached end effector 12 are inserted through the cannula passageway, the articulation mechanism 11 may be remotely articulated, as depicted in FIG. 2, by an articulation control 13. Thereby, the end effector 12 may reach behind an organ or approach tissue from a desired angle or for other reasons. For instance, a firing mechanism, advantageously depicted as an E-beam firing bar 14 (depicted in FIG. 3), that severs clamped tissue, engages an elongate channel 16 and a pivotally attached anvil 18.

The surgical and stapling and severing instrument 10 includes a handle portion 20 connected to an implement portion 22, the latter further comprising a shaft 23 distally terminating in the articulating mechanism 11 and the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

Thereafter, a release button 30 is depressed to release the clamped tissue.

An outmost closure sleeve 32 of the shaft 23 longitudinally translates in response to the closure trigger 26 to pivotally close the anvil 18. Specifically, a distal portion, or closure ring 33, of the closure sleeve 32 with respect to the articulation mechanism 11 is indirectly supported by a frame 34 of the implement portion 22 (partially visible at the articulation mechanism 11). At the articulation mechanism 11, a proximal portion, or closure tube 35, of the closure sleeve 32 communicates with the distal portion (closure ring) 33. The frame 34 is flexibly attached to the elongate channel 16 via the articulation mechanism 11, enabling articulation in a single plane. The frame 34 also longitudinally slidingly supports a firing drive member 36 that communicates a firing motion from the firing trigger 28 to the firing bar 14. Only the firing bar 14 of the firing drive member 36 is depicted FIG. 3, but the firing drive member 36 is described below further detail with regard to various versions of a rotationally controlled articulation mechanism 11.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

E-Beam Firing Bar

Figure 4:
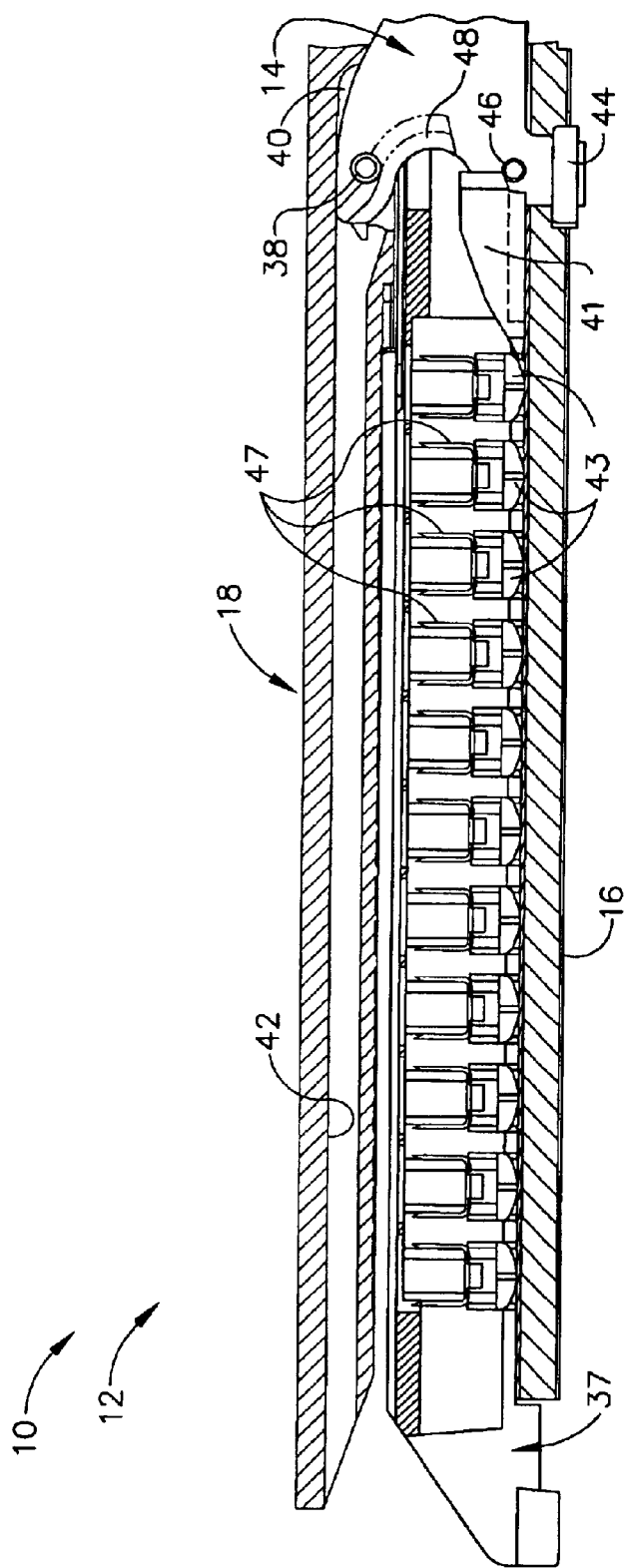
FIG. 4 depicts a side elevation view in section of the end effector of FIG. 3 of the surgical instrument of FIG. 1, the section generally taken along lines 4—4 of FIG. 3 to expose portions of a staple cartridge but also depicting the firing bar along the longitudinal centerline.
Figure 5:
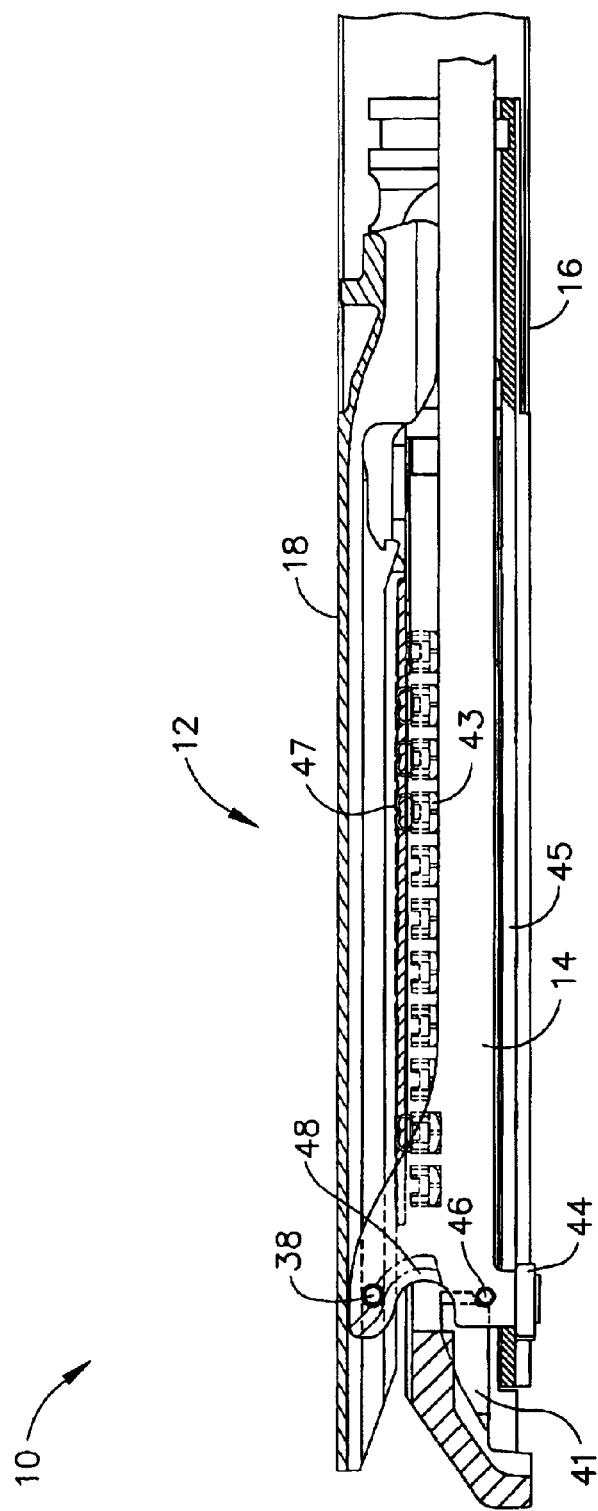
FIG. 5 depicts a side elevation view in section of the end effector of FIG. 4 after the firing bar has fully fired.

FIGS. 3–5 depict the end effector 12 employing the E-beam firing bar 14 to perform a number of functions. In FIG. 3, the firing bar 14 is proximally positioned, allowing an unspent staple cartridge 37 to be installed into the elongate channel 16. In particular, an upper pin 38 of the firing bar 14 resides within a recess, depicted as an anvil pocket 40 allowing the anvil 18 to be repeatedly opened and closed. With the end effector closed as depicted in FIG. 4, the firing bar 14 is advanced in engagement with the anvil 18 by having the upper pin 38 enter a longitudinal anvil slot 42. A lower most pin, or firing bar cap 44, engaged a lower surface of the elongate channel 16 by having the firing bar 14 extend through a channel slot 45. A middle pin 46 slidingly engages a top surface of the elongate channel 16, cooperating with the firing bar cap 44. Thereby, the firing bar 14 affirmatively spaces the end effector 12 during firing, overcoming pinching that may occur with a minimal amount of clamped tissue and overcoming staple malformation with an excessive amount of clamped tissue.

During firing, a distally presented cutting edge 48 between the upper pin 38 and middle pin 46 of the firing bar enters a proximally presented vertical slot 49 of the staple cartridge 37, severing tissue clamped between the staple cartridge 37 and the anvil 18. As shown in FIG. 4, the middle pin 46 actuates the staple cartridge 37 by entering into a firing slot within the staple cartridge 37, driving a wedge sled 41 into upward camming contact with staple drivers 43 that in turn drive a plurality of staples 47 out of staple apertures 51 in the staple cartridge 37 into forming contact with staple pockets 53 on an inner surface of the anvil 18. FIG. 5 depicts the firing bar 14 fully distally translated after completing severing and stapling tissue.

Two-Axis Handle

Figure 6:
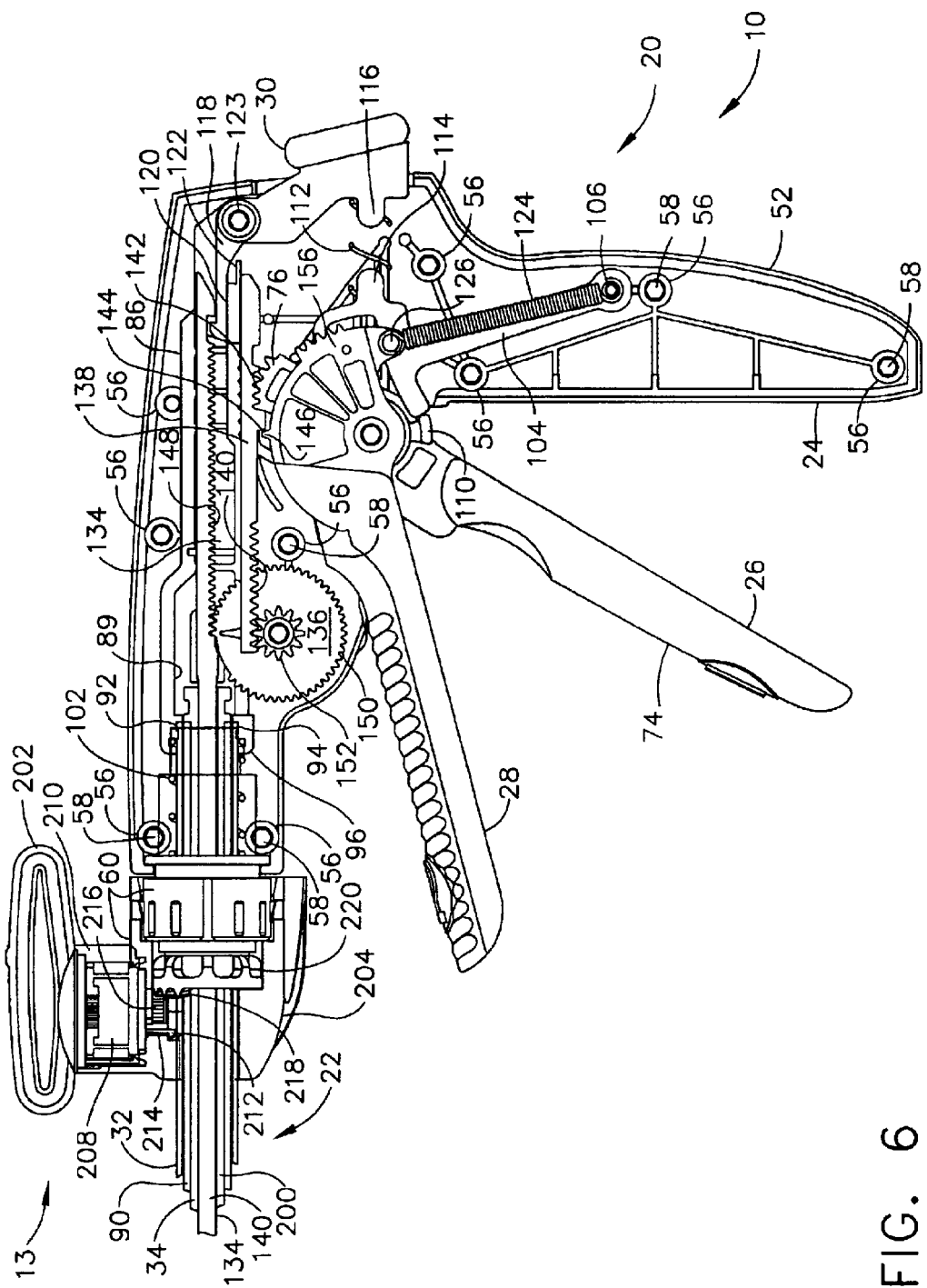
FIG. 6 depicts a side elevation view in section of a handle portion of a proximal end of the surgical instrument of FIG. 1 including a rotation-to-rotation ("rotational") articulation control.
Figure 7:
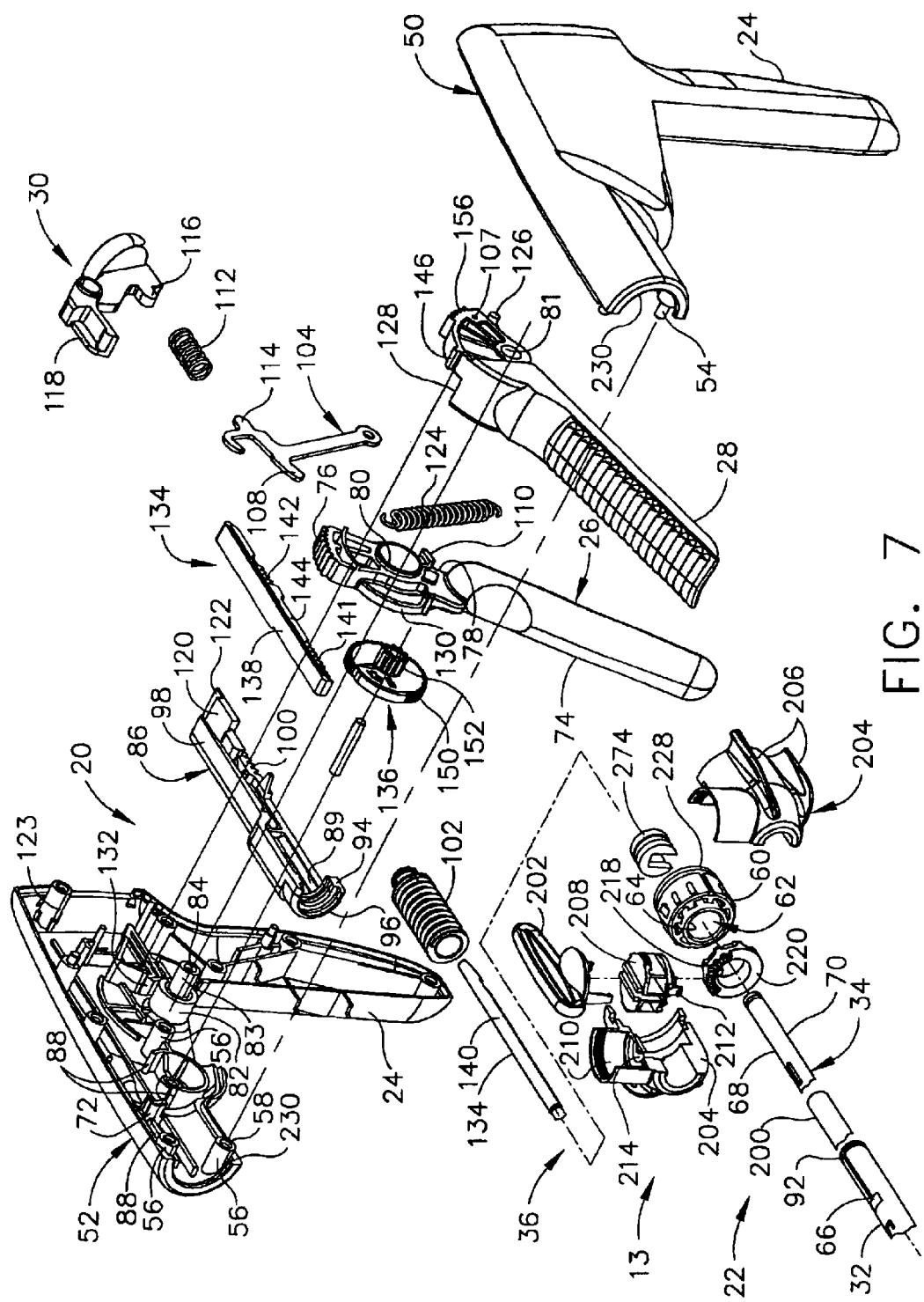
FIG. 7 depicts a perspective exploded view of the handle portion of the proximal end of the surgical instrument of FIG. 1.
Figure 8:
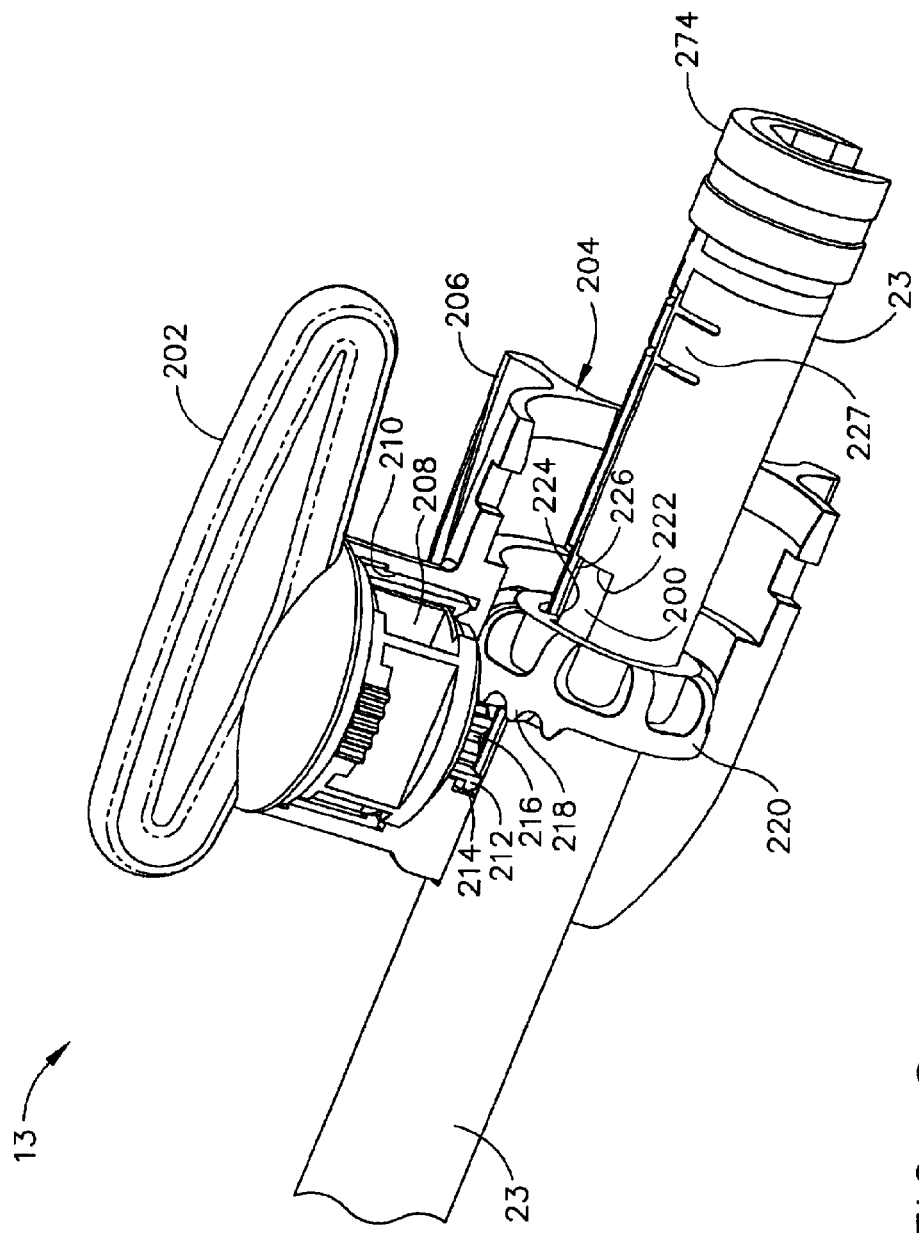
FIG. 8 depicts a perspective view looking downward, forward and to the right of a distal portion of the handle portion of the surgical instrument of FIG. 1 partially cutaway to expose a rotating articulation control mechanism.
Figure 9:
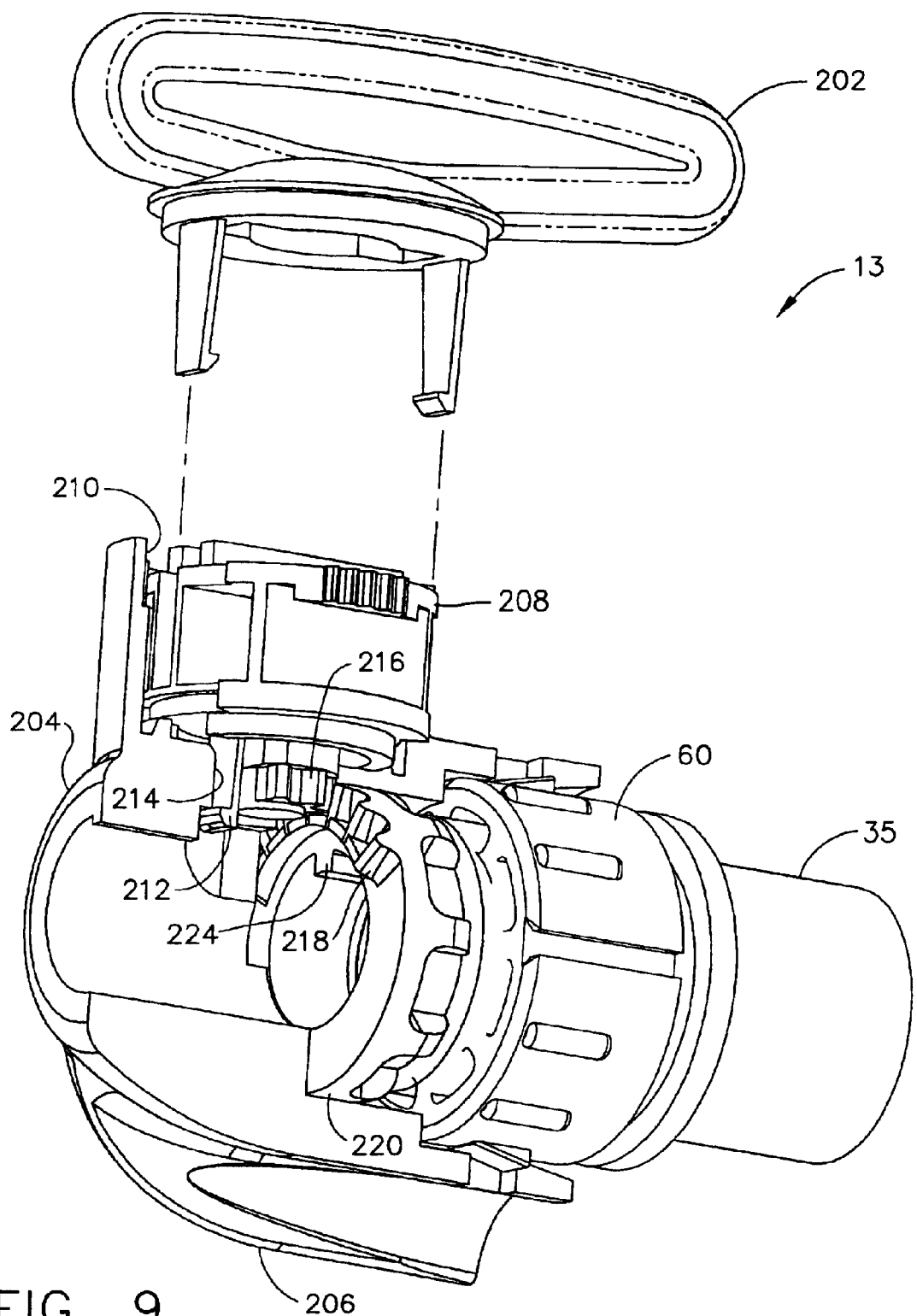
FIG. 9 depicts a perspective view looking upward, rearward and to the right of the distal portion of the handle portion of FIG. 8, partially cutaway to expose the rotating articulation control mechanism and have a rotating articulation control knob disassembled.

With reference to FIGS. 6–7, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A housing cap 60 has a bore 62 extending completely through it for engaging and rotating the implement portion 22 about its longitudinal axis. The housing cap 60 includes an inwardly protruding boss 64 extending along at least a portion of the bore 62. The protruding boss 64 is received within a longitudinal slot 66 formed at a proximal portion of the closure sleeve 32 such that rotation of the housing cap 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 3–4) rotates with the housing cap 60.

A proximal end 68 of the frame 34 passes proximally through the housing cap 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotally mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled, or wedge sled, in the implement portion 22 (not shown in FIG. 6–7) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter that is smaller than the first diameter.

Rotation-to-Rotation ("Rotational") Articulation Control of an Articulation Mechanism With reference to FIGS. 6–9, the handle portion 20 advantageously incorporates the articulation control 13 that both rotates the implement portion 22 about the longitudinal axis of the surgical instrument 10 and articulates the end effector 12 to an angle with the longitudinal axis. A hollow articulation drive tube 200 is concentrically located within the closure sleeve 32 and is operably coupled to an actuation lever 202 such that rotation of actuation lever 202 rotates tube 200 about the longitudinal axis and causes perpendicular rotation or articulation of the closure ring 250 and end effector 12. This articulation of the closure ring 250 corresponds to the degree and direction of rotation of actuator lever 202 viewed and manipulated by the clinician. In the illustrative version, the relationship is one to one, with the degree of rotation of the actuator lever 202 corresponding to the degree of articulation from the longitudinal axis of the shaft 23, thus providing an intuitive indication to the clinician. It will be appreciated that other angular relationships may be selected.

The articulation control 13 includes a pair of mirrored articulation transmission housings 204 that are attached to the housing cap 60. Moreover, the articulation transmission housing 204 includes longitudinally aligned external tabs 206 that a clinician twists to effect rotation of the articulation transmission housing 204, and thus of the end effector 12, about the longitudinal axis of the implement portion 22. The actuator lever 202 is attached to a cylindrical articulation body 208 that resides within a cylindrical recess 210 opening generally upward and perpendicular to the shaft 23. The lowermost portion of the articulation body 208 includes prongs 212 that snap fit into an opening 214 in the articulation transmission housing 208 near to the shaft 23, the prongs 212 preventing the articulation body 208 from being withdrawn from the cylindrical recess 210.

Annularly presented gear teeth 216 are located about the lower portion of the articulation body 208 and mesh with teeth 218 on an articulation yoke 220. The articulation yoke 220 straddles an articulation rectangular window 222 formed in the closure sleeve 32. Closure sleeve 32 is slidably moveable within the articulation control 13 (in the longitudinal direction) to close and open the end effector 12. The articulation drive tube 200 moves longitudinally with the closure sleeve 32 relative to the fixed articulation control 13. Window 222 provides clearance for a boss 224 inwardly presented from the articulation yoke 220 that passes through the rectangular window 222 to engage a slot 226 in the articulation drive tube 200, longitudinally positioning the articulation drive tube 200 for rotational motion. The hollow articulation drive tube 200 extends longitudinally within the closure sleeve 32 from the articulation mechanism 11 and terminates distally before the locking tabs 227 of the closure sleeve 32. The tabs 227 are inwardly bent behind the proximal face of the articulation drive tube 200 and thereby retaining the articulation drive tube 200 in the shaft 23.

It should be appreciated that the articulation transmission housing 204 is operatively associated to the closure tube 35 of the shaft 23. The housing cap 60 retains the articulation yoke 220 in the articulation transmission housing 204 and retains the articulation control 13 within the handle portion 20 by presenting proximally an outer diameter circular groove 228 that engages a circular inward lip 230 at the distal opening of the assembled base sections 50, 52.

Figure 10:
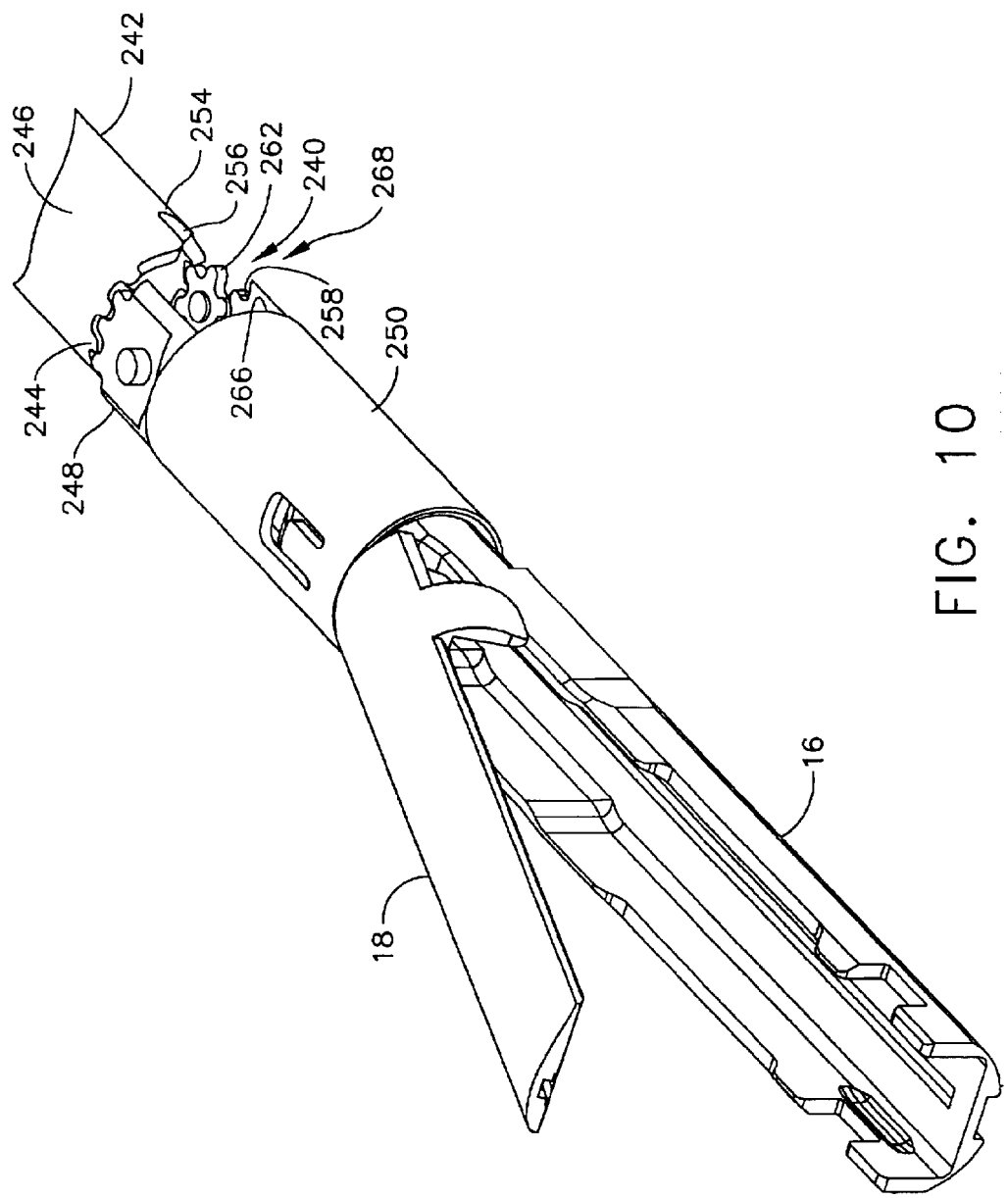
FIG. 10 depicts a top perspective detail view of a spur gear articulation mechanism and end effector of the surgical instrument of FIG. 1 with firing and frame portions removed.
Figure 11:
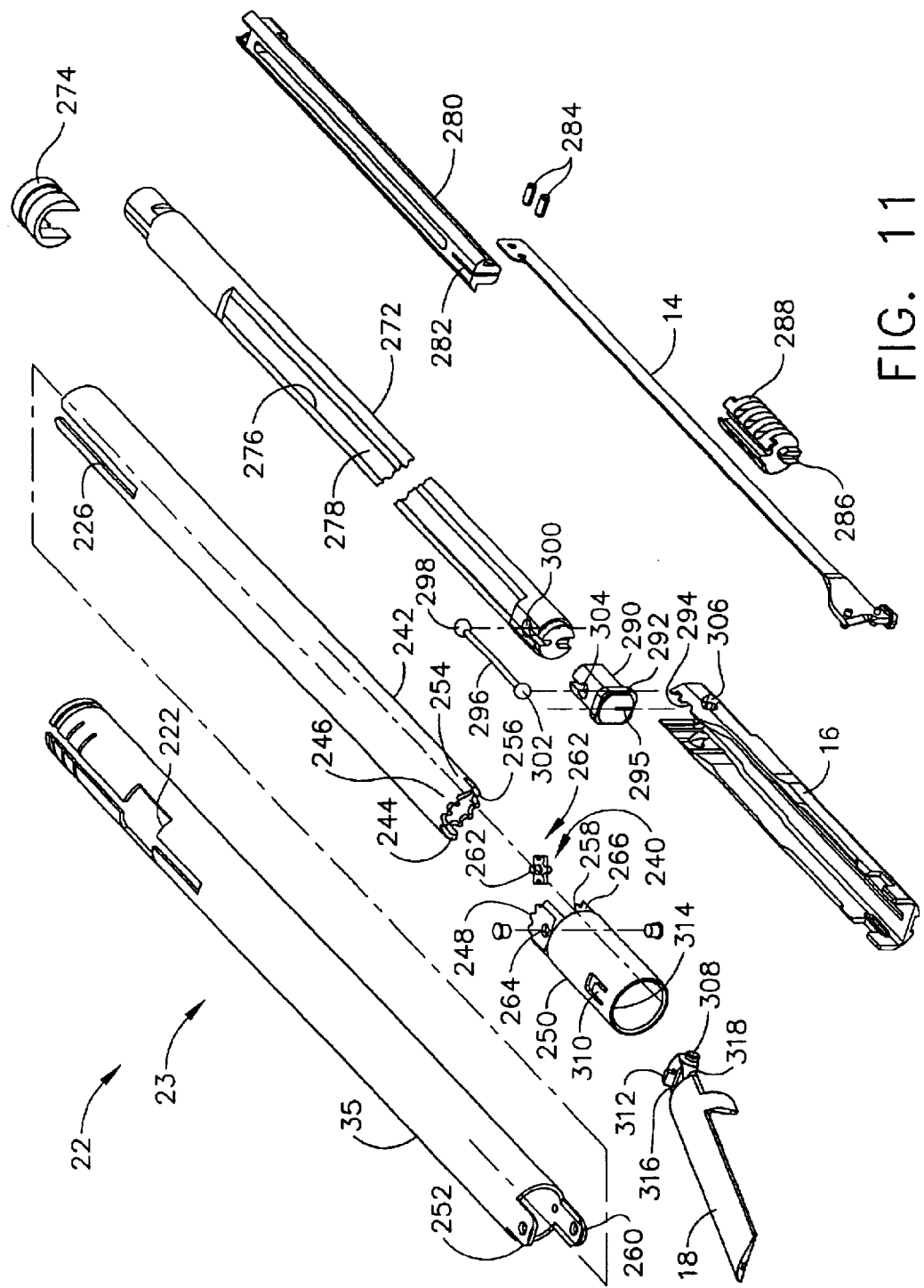
FIG. 11 depicts a perspective, exploded view of an implement portion of the surgical instrument of FIG. 1 including a spur gear articulation mechanism.

FIGS. 10 and 11 depict the gear articulation mechanism 11 of FIGS. 1–2 in the form of a spur gear articulation mechanism 240, which is generally the same as described above but with additional articulation driving components on the other side of the articulation mechanism 240 to thereby increase performance. Articulation mechanism 240 has a rotatable hollow articulation drive tube 242 that is concentrically located within closure sleeve 32 and has a distally projecting gear section 244 about a first circumference portion 246. Gear section 244 meshes with a spur gear 248 attached to and proximally projecting from closure ring 250 which pivots about pins 253 extending through first and second pivot points 252, 260 projecting distally from the closure sleeve 32. Thus, an articulation pivot axis passes through both the first and second pivot points 252, 260 and pins 253 rotatably couple closure ring 250 to the closure sleeve 32. Rotation of drive 242 engages the gears 242 and 248 and articulates closure ring 250 about first and second pivot points 252, 260.

To increase the effective surface area of gear contact between the hollow articulation drive tube 242 and the closure ring 250, a second circumference portion 254 of the hollow articulation drive tube 242 has a recessed distally projecting gear section 256 extending therefrom. Gear section 256 is operably coupled to a second spur gear 258 attached to and proximally projecting from an opposite lateral side of the closure ring 250 by a reversing gear 262 pivotally supported by the frame 34. Reversing gear 262 engages both the recessed distally projecting gear section 256 on one side and the second spur gear 258 of the closure ring 250 on the other.

When the closure trigger 26 is actuated, both the hollow articulation drive tube 242 and pivotally attached closure tube 250 of the closure sleeve 32 are moved distally to close the anvil 18. The closure tube 35 of the closure sleeve 32 is spaced away from the closure ring 33 by pivot points 252, 260 pinned to pivot holes 264 and 266 centered in spur gears 248, 258, and a frame opening 268 that extends therethrough. The frame opening 268 provides clearance so that the proximal edges of the closure ring 33 and the distal edges of the closure tube 35 of the closure sleeve 32 do not collide during articulation.

FIG. 11 depicts in disassembled form an implement portion 270 that includes the spur gear articulation mechanism 240. A frame 272 is longitudinally attachable to the handle portion 20 (depicted in FIGS. 1 and 2) with a bushing 274 on its proximal end for rotatingly engagement thereto. A frame trough 276 formed by an opening 278 longitudinally aligned with the center of the frame 272 is longer than a firing connector 280 that slides longitudinally within the frame trough 276. The proximal end of the firing connector 280 rotatingly engages the distal end of the metal drive bar 140 (depicted in FIG. 6). The distal end of the firing connector 280 includes a slot 282 that receives a proximal end of the firing bar 14, attached therein by pins 284. A more distal portion of the firing bar 14 is positioned within a lower groove 286 in a firing bar slotted guide 288 that is distally engaged with an articulating frame member 290 and the frame 272.

Articulating frame member 290 has a channel-anchoring member 292 that distally attaches to an attachment collar 294 of a proximal portion in the elongate channel 16. The firing bar 14 passes through a lower slot 295 in the articulating frame member 290. The articulating frame member 290 is spaced away from the distal end of the frame 272 by the firing bar slotted guide 288 and flexibly attached thereto for articulation by a resilient connector 296. A widened proximal end 298 of the resilient connector 296 engages a distally communicating top recess 300 in the distal end of the frame 272 and a widened distal end 302 of the resilient connector 296 engages a proximally communicating top recess 304 in the articulating frame member 290. Thereby, the elongate channel 16 is attached to the handle portion 20, albeit with a flexible portion therebetween.

The elongate channel 16 also has an anvil cam slot 306 that pivotally receives an anvil pivot 308 of the anvil 18. The closure ring 250 that encompasses the articulating frame member 290 includes a distally presented tab 310 that engages an anvil feature 312 proximate but distal to the anvil pivot 308 on the anvil 18 to thereby effect opening. When the closure ring 250 is moved forward, its distally presented closing face 314 contacts a ramped cylindrical closing face 316, which is distal to tab 312 of the anvil 18. This camming action closes the anvil 18 downward until the closing face 314 of the closure ring 250 contacts a flat cylindrical face 318 of the anvil 18.

Lateral-to-Longitudinal Articulation Control of an Articulation Mechanism

Figure 12:
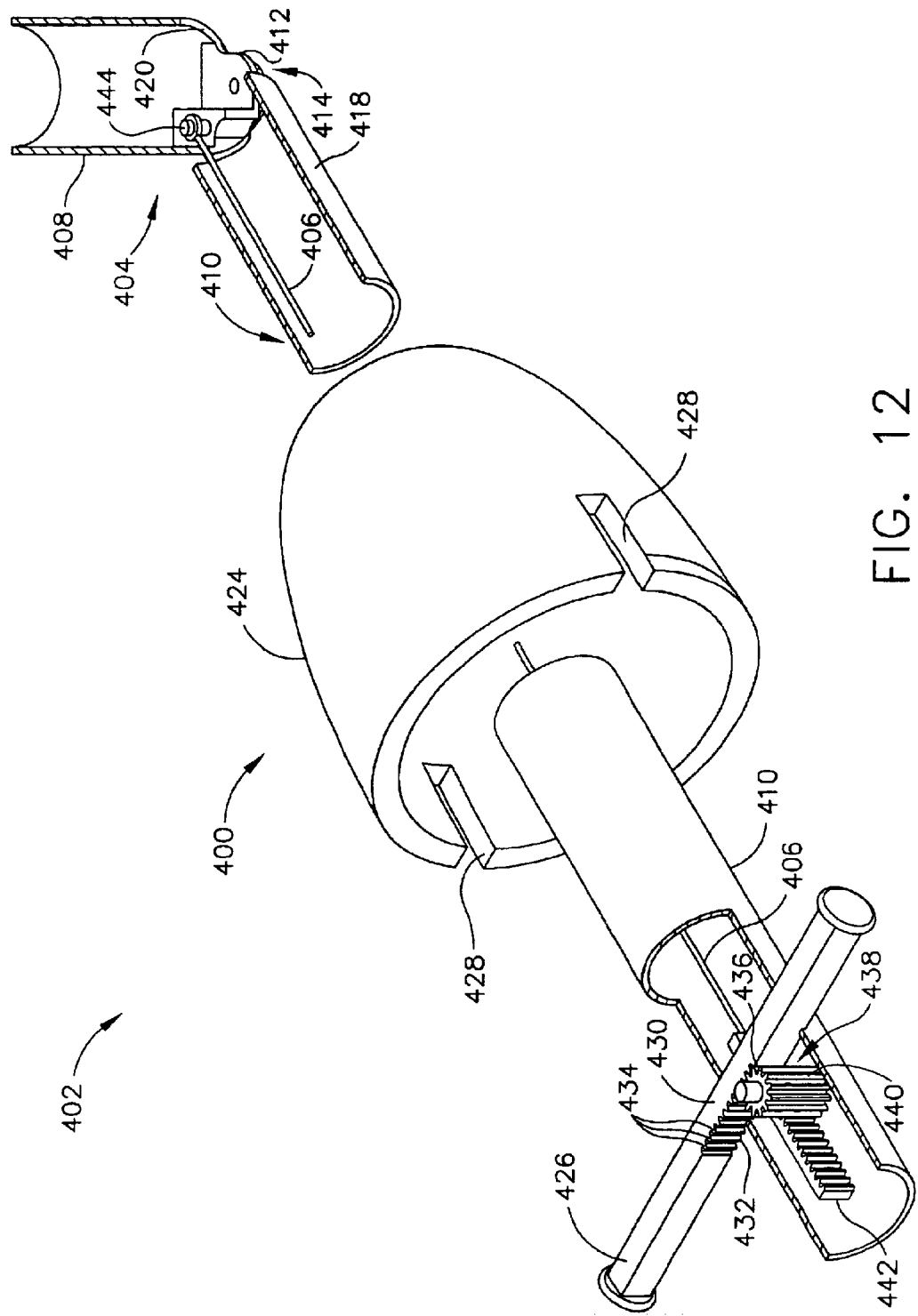
FIG. 12 depicts a perspective view looking downward, forward and to the right of a distal portion of the handle portion of the surgical instrument of FIG. 1 partially cutaway to expose a lateral-to-longitudinal articulation control mechanism as an alternative to the rotating articulation control mechanism of FIGS. 1, 2, and 6–9.
Figure 13:
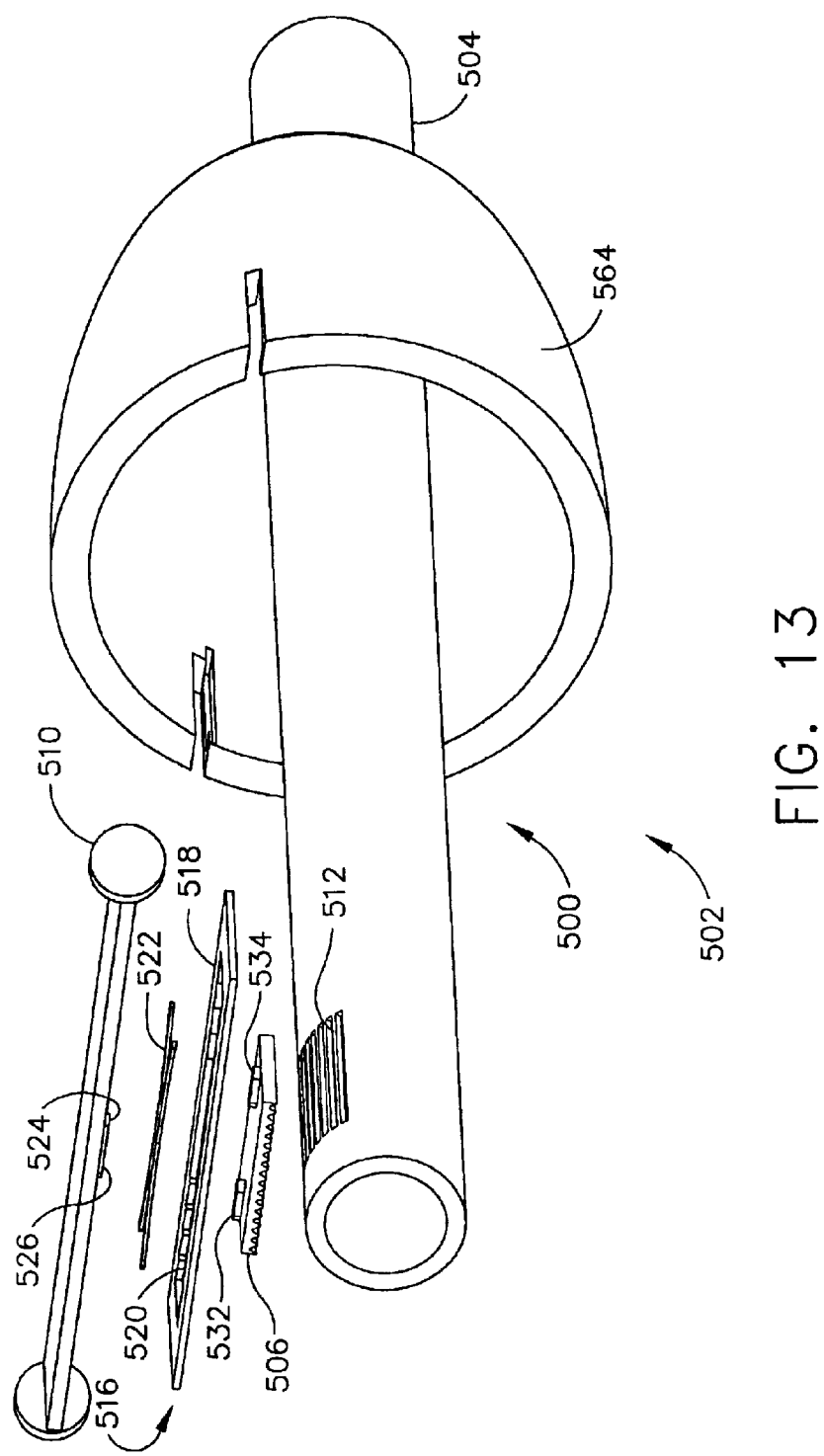
FIG. 13 depicts a perspective, exploded view of a lateral-to-rotation articulation control mechanism as an alternative to the lateral-to-longitudinal articulation control mechanism of FIG. 12.

FIG. 12 illustrates a lateral articulation control 400 for a surgical instrument 402 that incorporates an articulation mechanism 404 pivoted by a longitudinal motion from an articulation control rod 406 as an alternative to the rotational articulation control of FIGS. 6–9. Approaches to articulating a surgical stapling and severing instrument tend to be complicated by integrating control of the articulation alone with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions. Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. An end effector 408 is connected to a shaft assembly 410 by a pivot 412 in a manner similar to that described above but without a gear capability and a rotating articulation drive tube. Thus only one pivot 412 is shown but it will be appreciated that another pivot is formed along the axis of the first pivot 412, thereby connecting the other lateral sides of the end effector 408 and shaft assembly 410. An articulation opening 414 is formed by having the pivot 412 extended away from the circumference of both a distal end 418 of the shaft assembly 410 and a proximal end 420 of the end effector 408. The size of the articulation opening 414 is radially sized about each lateral side of the pivot axis for the desired maximum allowed amount of articulation.

A knob 424 is shown distally removed from the shaft assembly 410 to expose a lateral control actuator 426 that extends laterally through openings 428 on both sides of the knob 424. A central portion 430 of the lateral control actuator 426 has a proximally directed teeth rack 432 with vertically aligned teeth 434 that engage an upper portion 436 of a vertically-aligned elongate gear 438. A lower portion 440 of the vertically aligned elongate gear 438 engages a right-facing gear rack 442 connected proximally to the articulation control rod 406.

Thus, as the lateral control actuator 426 is moved laterally to the left, its proximally directed teeth rack 432 rotates the elongate gear 438 counter clockwise, as viewed from the top, thereby moving the right-facing gear rack 442 proximally, drawing the articulation control rod 406 proximally. Thereby, the end effector 408 is articulated to the left since the articulation control rod 406 attaches at a pin 444 on the proximal end 420 of the end effector to the left of the pivot 412.

It will be appreciated that various other lateral-to-longitudinal gear mechanisms may be employed. For instance, having both gear racks 432, 442 engage the elongate gear 438 from opposite sides with respect to their respective engagements that are depicted would accomplish a like result. Moreover, reversing the engagement in only one of the two could be done in conjunction with reversing the attachment of the longitudinal control rod 406 from the left of the pivot 412 to the right. As yet a further alternative, switching one of these three orientation or all three to their respective opposite configuration may inverse the control, articulating the end effector 408 in an opposite direction as the lateral control actuator 426.

It should be further appreciated that the depicted lateral-to-longitudinal gear mechanism creates a degree of articulation that is related to the distance of a pivoting connection at pin 444 of the longitudinal control rod 406 to the end effector 408 normal to the pivot axis. Varying this amount of articulation travel relative to the movement of the lateral control actuator 426 may be achieved by gear relationship between the gear rack 432 of the lateral control actuator 426 and the gear rack 442 connected to the longitudinal control rod 406. For instance, the elongate gear 438 may have an upper portion having a diameter that differs from the diameter of the lower portion.

Lateral-to-Rotational Control of an Articulation Mechanism

FIGS. 13–16 depict a lateral-to-rotational articulation control 500 that provides similar intuitive clinician control features as does the lateral-to-longitudinal articulation control 400 of FIG. 12 for an articulating surgical instrument 502 that is similar to that described for FIGS. 1–11. In particular, the lateral articulation control 500 converts a lateral motion into a rotational motion transferred by an articulation drive tube 504 to an articulation mechanism (not shown in FIGS. 13–16 ). A downward projecting gear rack 506 is coupled to a lower side 508 of a lateral control actuator 510 for engaging with longitudinally aligned grooves 512 on a top face of the articulation drive tube 504.

An articulation backdrive lockout 516 is advantageously incorporated into the lateral articulation control 500 to prevent a force upon the end effector (not depicted in FIGS. 13–16) from changing the amount of articulation. In particular, interposed between the articulation control actuator 510 and the gear rack 506 is a rack plate 518 that includes a central opening 520 containing a flexible X-shaped locking member 522. The articulation control actuator 510 includes two deflection blades 524, 526 that downwardly project into the central opening 520 of the rack plate 518 and are positioned respectively in a distal and a proximal quadrant defined by the X-shaped locking member 522 with respect to a top view depicted in FIGS. 15-16. The gear rack 506 includes two drive blades 532, 534 that upwardly project into the central opening 520 of the rack plate 518 and are positioned respectively in the left and right quadrants 536, 538 defined by the X-shaped locking member 522. The central opening 520 of the rack plate 518 is shown as being generally rectangular in shape, but with ramped teeth 540, each presenting an abutting surface 542 inwardly facing and longitudinally aligned. These ramped teeth 540 are placed along a right and left portion 544, 546 of a distal edge 548 to ratchedly contact right and left distal arms 550, 552 respectively of the X-shaped locking member 522. The ramped teeth 540 are also placed along a right and left portion 554, 556 of a proximal edge 558 of the rectangular window 520 to ratchedly contact right and left proximal arms 560, 562 of the X-shaped locking member 522.

Figure 14:
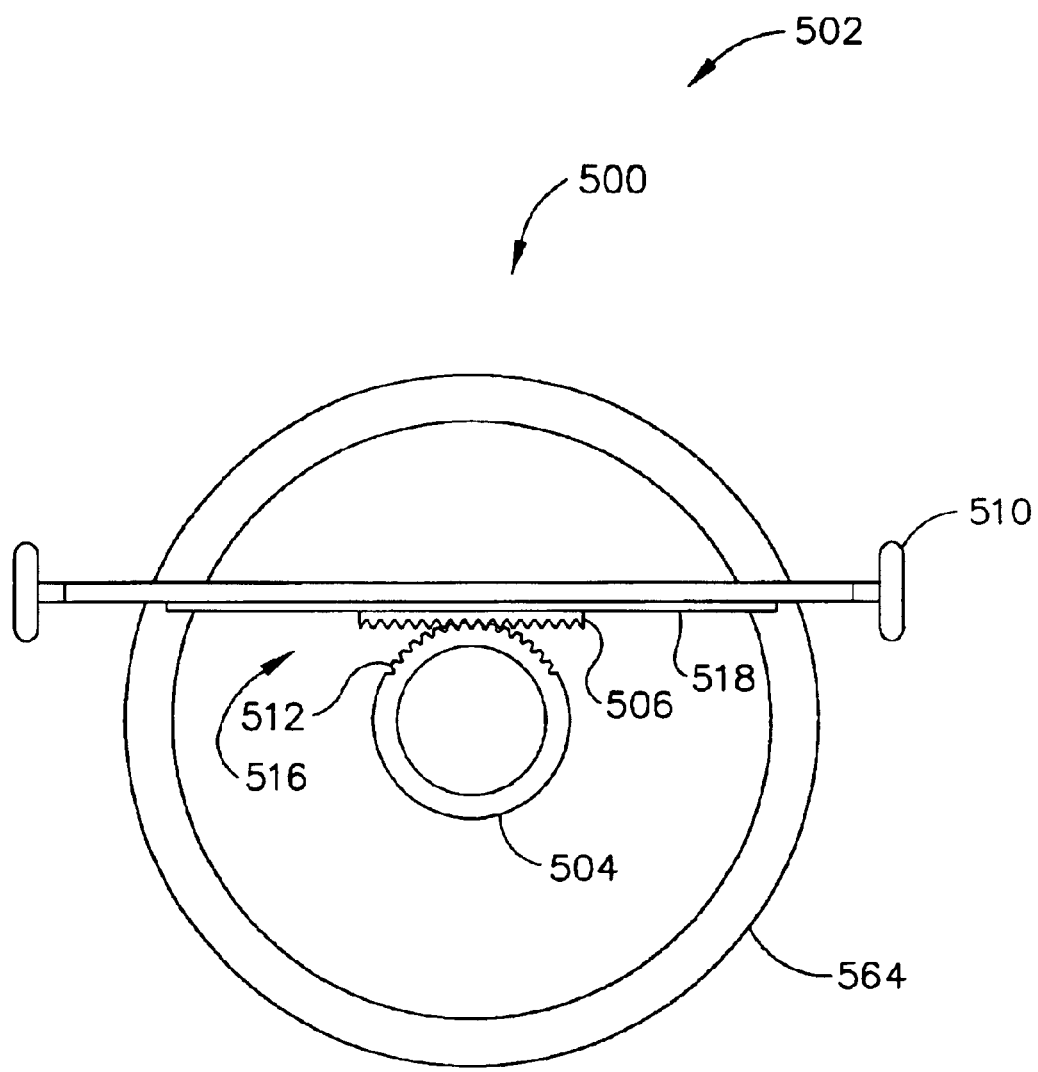
FIG. 14 depicts a front elevation view in section of the lateral-to-rotation articulation control mechanism of FIG. 13.

With particular reference to FIG. 14, the gear rack 518 is illustrated as attached to a knob 564 and thus does not laterally translate with the articulation control actuator 510 or the gear rack 506. Lateral movement of the articulation control actuator 510 is transferred through the articulation backdrive lockout 516 formed inside the rectangular window 520 of the rack frame 518. By contrast, a backdriven lateral movement of the articulation drive tube 504 and hence the gear rack 506 is reacted by the articulation backdrive lockout 516 into the rack frame 518 and into the knob 560. Thus movement of the articulation drive tube 504 is arrested.

Figure 15:
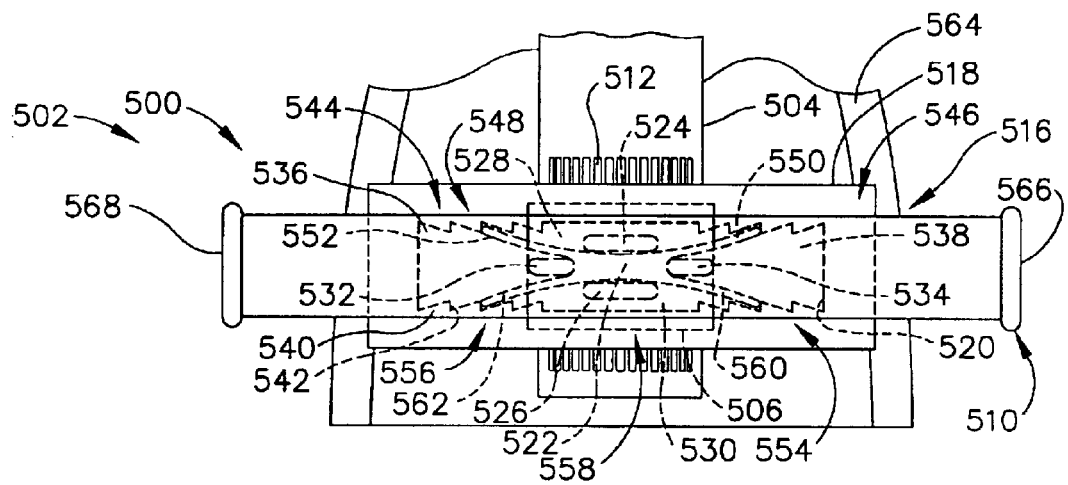
FIG. 15 depicts a detail view of a locking block in an engaged state of the lateral-to-rotation articulation control mechanism of FIG. 13.

In use, as depicted in FIG. 15, the lateral articulation control 500 is centered. Thereby, a visual indication is given to the clinician by the equally extended left and right ends 566, 568 of the articulation control actuator 510. The deflection blades 524, 526 are centered on the X-shaped lockout member 522, exerting no force on the arms 550, 552, 560, 562, which are thereby allowed to extend toward their uncompressed state into abutting contact with the ramped teeth 540, preventing lateral movement of the X-shaped lockout member 522. The drive blades 532, 534 of the gear rack 506 are in opposing contact on each side of the X-shaped lockout member 522. Any lateral force transferred from the articulation drive tube 504 into the gear rack 506 through the drive blades 532, 534 is reacted through the X-shaped lockout member 522 into the gear rack 506, preventing movement.

Figure 16:
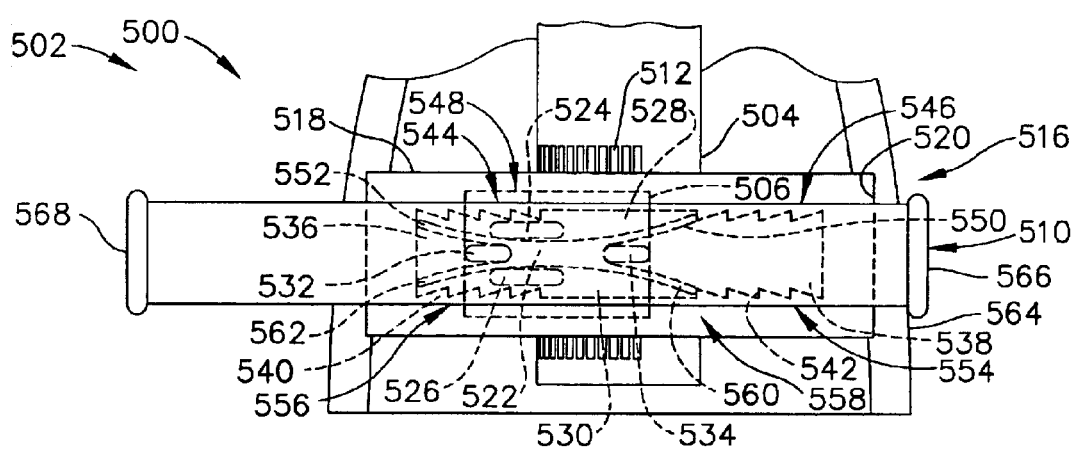
FIG. 16 depicts a detail view of the lateral-to-rotation articulation control mechanism of FIG. 13 in a disengaged state.

By contrast, as depicted in FIG. 16, when a clinician moves the articulation control actuator 510 to one lateral side, the deflection blades 524, 526 contact a pair of proximal and distal arms (the left ones 552, 562 in FIG. 16) compressing the pair away from contact with the rectangular window 520. Thus, the X-shaped lockout member 522 is allowed to move in that direction with the trailing pair of arms (e.g., right ones 550, 560 in FIG. 16) ratcheting along. This lateral movement is allowed to continue until the leading arms 552, 562 encounter the lateral extend of the rectangular window 520 as depicted. The drive blades 532, 534 of the gear rack 506 move with the X-shaped lockout member 522 and thus ultimately the end effector (not shown in FIG. 16) also articulates in response.

The present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For yet another example, although an illustrative handle portion 20 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

As yet an additional example, although a simultaneous stapling and severing instrument is advantageously illustrated herein, it would be consistent with aspects of the invention rotationally controlled articulation with other types of end effectors, such as grasper, cutter, staplers, clip applier, access device, drug/gene therapy delivery device, and a energy device using ultrasound, RF, laser, etc.

What is claimed is:

1. A surgical instrument, comprising:
   an end effector;
   a shaft having a longitudinal axis and including an articulation motion transfer member operatively configured to transfer an articulation motion;
   an articulation mechanism responsive to the articulation motion from the articulation motion transfer member and pivotally coupling the end effector to a distal end of the shaft in a single plane bisected by the longitudinal axis to articulate selectively in a first direction and a second direction; and
   an articulation control coupled to a proximal portion of the shaft, comprising:
      an actuator laterally and linearly positionable by a user, a lateral motion therefrom aligned to the single plane to correspond to the selected one of the first and second direction of articulation, and
      a motion conversion mechanism coupled to the actuator and to the articulation mechanism and operably configured to convert the lateral motion from the articulation control to an articulation motion.

2. The surgical instrument of claim 1, wherein the shaft further comprises an articulation drive tube transferring the articulation motion as a rotational motion to the articulation mechanism.

3. The surgical instrument of claim 2, wherein the motion conversion mechanism comprises a gear means for coupling the lateral movement to the rotational motion.

4. A surgical instrument, comprising:
   an end effector;
   a shaft including an articulation motion transfer member operatively configured to transfer an articulation motion;
   an articulation mechanism responsive to the articulation motion and pivotally coupling the end effector to a distal end of the shaft; and
   an articulation control coupled to a proximal portion of the shaft, comprising:
      an actuator laterally positionable by a user,
      a longitudinal control rod coupled to the end effector at an attachment offset from a pivot axis of the articulation mechanism, and
      a motion conversion mechanism coupled to the actuator and to the articulation mechanism operably configured to convert a lateral motion from the articulation control to a longitudinal motion.

5. The surgical instrument of claim 4, wherein the motion conversion mechanism comprises a gear means for coupling the lateral movement to the longitudinal motion.

6. The surgical instrument of claim 4, wherein the motion conversion mechanism comprises:
   a lateral gear rack coupled to the articulation control;
   a gear engaged to the gear rack of the articulation control; and
   a longitudinal gear rack coupled to the longitudinal control rod and engaged to the gear.

7. A surgical instrument, comprising:
   an end effector;
   a shaft including an articulation drive tube having a gear section for transferring an articulation rotational motion;
   an articulation mechanism responsive to the articulation rotational motion and pivotally coupling the end effector to a distal end of the shaft; and
   an articulation control coupled to a proximal portion of the shaft, comprising:
      an actuator laterally positionable by a user, and
      a motion conversion mechanism comprising a lateral gear rack coupled to the actuator and to the gear section of the articulation drive tube to convert a lateral motion from the actuator to the articulation rotational motion.

8. The surgical instrument of claim 7, wherein the motion conversion mechanism further comprises a backdrive lockout mechanism coupling the actuator to the lateral gear rack.

9. The surgical instrument of claim 8, wherein the backdrive lockout mechanism comprises:
   a frame having a window;
   a lockout member laterally locked into position with the window of the frame and coupled to the lateral gear rack; and
   a deflection member coupled to the articulation control and positioned to disengage and to laterally position the lockout member.

10. The surgical instrument of claim 8, wherein the backdrive lockout mechanism comprises a means for preventing transferring motion from the articulation drive tube to the articulation mechanism.

11. A surgical instrument, comprising:
   a shaft configured to independently transfer an actuating motion, and a rotational motion about a longitudinal axis thereof;
   an end effector responsive to the actuating motion;
   an articulation mechanism responsive to the rotational motion to articulate the end effector from the longitudinal axis of the shaft;
   a handle portion coupled to the shaft operably configured to produce the actuating motion;
   a lateral articulation control laterally positionable by a user and operably configured to produce the rotational motion, wherein the lateral articulation control further comprises a backdrive lockout mechanism.

12. A surgical instrument, comprising:

a handle portion operable to produce a firing motion, a closing motion, and an articulation motion;

a shaft coupled to the handle portion operable to separately transfer the firing motion, the closing motion, and the articulation motion;

an elongate channel coupled to the shaft;

an anvil pivotally coupled to the elongate channel, responsive to the closing motion from the shaft;

a firing device including a distally presented cutting edge longitudinally received between the elongate channel and the anvil;

an articulation mechanism pivoting the elongate channel from the shaft in response to the articulation motion; and a lateral articulation control laterally positionable by a user and operably configured to produce the articulation motion, wherein the lateral articulation control further comprises a backdrive lockout mechanism.

13. A surgical instrument, comprising:

a shaft defining a longitudinal axis of the surgical instrument;

an end effector movable from a first position in alignment with said longitudinal axis to a second position at an angle in a single plane with said longitudinal axis;

a rotatable member operably coupled with said end effector such that rotation of said member moves said end effector from said first to said second position; and a lateral control member moveable laterally and linearly to said longitudinal axis in corresponding alignment with the single plane formed by the end effector in moving between first and second positions and operably coupled to said rotatable member, wherein lateral movement of said lateral control member moves said end effector from said first to said second position.

* * * * *